United States Patent [19]

Sandridge et al.

[11] Patent Number: 4,795,253

[45] Date of Patent: Jan. 3, 1989

[54] REMOTE SENSING GAS ANALYZER

[75] Inventors: Robert L. Sandridge, Proctor; Robert N. Hunt, Wheeling, both of W. Va.

[73] Assignee: Mobay Corporation, Pittsburgh, Pa.

[21] Appl. No.: 42,121

[22] Filed: Apr. 24, 1987

[51] Int. Cl.$^4$ ................................................. G01J 3/45
[52] U.S. Cl. ................................... 356/51; 250/338.5; 356/346
[58] Field of Search .......................... 356/305, 346, 51; 250/343, 338.5

[56] References Cited

U.S. PATENT DOCUMENTS

| | | | |
|---|---|---|---|
| 3,363,525 | 1/1968 | Teeple, Jr. | 356/305 X |
| 3,766,380 | 10/1973 | Menzies | 250/343 |
| 3,925,666 | 12/1975 | Allan et al. | 250/338 |
| 3,931,462 | 1/1976 | Eaton | 356/439 X |
| 4,286,877 | 9/1981 | Clarke | 356/346 |
| 4,490,043 | 12/1984 | Cramp | 356/407 |
| 4,529,317 | 7/1985 | Cramp | 356/407 |
| 4,650,321 | 3/1987 | Thompson | 356/305 X |

OTHER PUBLICATIONS

Herget et al., "Remote Fourier Transform Infrared Air Pollution Studies", Optical Engineering, vol. 19, pp. 508-514, Jul./Aug., 1980.
Herget et al., "Remote and Gross-Stack Measurement of Stack Gas Concentrations Using a Mobile FT-IR System", Applied Optics, vol. 21, pp. 635-641, 2/15/82.

Primary Examiner—Davis L. Willis
Assistant Examiner—Matthew W. Koren
Attorney, Agent, or Firm—Gene Harsh; Joseph C. Gil; Lyndanne M. Whalen

[57] ABSTRACT

A particular area or areas are monitored for the presence of gaseous materials, particularly pollutants by collecting background radiation (both visible and infrared radiation) present in the selected area, analyzing the radiation collected with a spectrometer and making the results of this analysis available is a form understandable to the person or device moitoring the area for the presence of specified gaseous materials. The results of the spectrometric analysis may, for example, be displayed on a video unit or they may be printed. In a preferred embodiment, the results of the spectrometric analysis are displayed on a video unit simultaneously or sequentially with the image of the area from which the background radiation had been collected. Apparatus useful in the practice of this invention generally includes large energy collecting mirrors, an interferometer of the Michaelson-Morely type, a sensitive infrared detector, electronic data processing, and a device which records and/or displays the results of the determination(s). In a preferred apparatus, a "hot" mirror, a video camera, a computer and a video display unit are also employed.

43 Claims, 4 Drawing Sheets

REMOTE SENSING GAS ANALYZER

BACKGROUND OF THE INVENTION

The present invention relates to a method for detecting gaseous materials present in the atmosphere of a selected area and to apparatus useful therefor.

In production facilities, particularly chemical production facilities, potentially hazardous materials are often employed. To reduce the risk of production, handling and use of such materials, detection of the presence of their vapors in the atmosphere before dangerous levels are reached is desirable. Continuous monitoring of the atmosphere of the production facilities is one way to ensure early detection of undesirable materials in the atmosphere.

Many approaches for monitoring the atmosphere for the presence of pollutants have been explored. U.S. Pat. No. 3,766,380 and U.S. Pat. No. 3,925,666 for example, disclose methods in which an infrared laser beam is transmitted through the atmosphere. The reflections of this transmitted laser beam are collected and analyzed for information relating to the presence of gaseous pollutants. In each of these disclosed methods, the wavelength of the transmitted laser beam must be chosen to detect a specific gaseous pollutant. Consequently, a second different pollutant could be detected on the same device and discriminated from the first pollutant only if a laser beam having a wavelength different from that used to detect the first pollutant were used. It would not therefore be possible to continuously monitor the atmosphere for several hazardous materials with a single device by the process disclosed in these two patents. In fact, continuous monitoring for more than one pollutant would be possible only by using as many devices as there are gaseous pollutants possible in the monitored area.

U.S. Pat. Nos. 4,490,043 and 4,529,317 each disclose a method for monitoring gaseous pollutants in which multiple transmitted laser beams are employed. In U.S. Pat. No. 4,490,043, two laser beams at different frequencies are employed. One beam has a wavelength specific to the gas or gases being monitored and the other beam is a reference beam at a nearby wavelength which does not have absorption bands from the pollutant or other compounds. This method is limited to detection of a specific pollutant or pollutants whose presence in the environment is expected. Further, this method requires variation of the amount of radiation reaching the detector in order to prevent overload to the detector when the beam scans areas of high reflectivity, thus limiting the quantitative capabilities of the device. Furthermore, this method gives only the direction of the gas and not the distance of a gas cloud.

In the monitoring method disclosed in U.S. Pat. No. 4,529,317, at least two scanning beams, each containing multi-plexed reference and measuring wavelengths are directed towards the location to be monitored from two spaced apart scanning positions. Combination of information from the two signals provides a measure of the amount of gas at the intersection of the two beams. As in the method disclosed in U.S. Pat. No. 4,490,043, the reference beam wavelength is selected on the basis of the particular pollutant expected to be present in the environment. Continuous monitoring for the presence of more than one pollutant can not therefore be accomplished with a single device.

In each of the above-described systems and any other infrared laser-based systems, only a limited number of discrete wavelengths can be generated by the laser and used for measuring and reference beams. The available wavelengths may not however be well matched to the absorption peaks of interest resulting in lower sensitivity of the system and increasing the likelihood of interference from other pollutants. In addition, since only one measuring wavelength is normally considered, any other compound which absorbs at the selected frequency would give a signal which would be indistinguishable from the signals given by the pollutant of interest. Interference in the measurement of the pollutant being monitored would result.

The Environmental Protection Agency has pursued methods for monitoring the atmosphere for gaseous pollutants which would not be limited to detection of only one compound at a time. A brief history of the Environmental Protection Agency's attempts to use remote optical sensing of emissions (ROSE) systems in which commercial Fourier Transform infrared spectrophotometers are used is given by Herget et al in "Remote Fourier Transform Infrared Air Pollution Studies," *Optical Engineering,* Volume 19, No. 4, pages 508-514 (July/August 1980). Herget et al also describes an improved mobile ROSE system in this article. Actual tests conducted with this improved mobile system are described in Herget's "Remote and Cross-stack Measurement of Stack Gas Concentrations Using a Mobile FTIR System" in *Applied Optics,* Vol. 21, No. 4, pages 635-641 (Feb. 15, 1982).

One of the EPA's first ROSE systems was a mobile system designed to detect and measure pollutants present at various pollution sources from a point remote from the pollution source. In this system, interferograms collected in the field were returned to a central computer for processing. This delay between data collection and data processing was undesirable because it made it difficult, if not impossible, to detect a leak before it had spread and created a potentially hazardous condition. This early system was subsequently improved to permit on-site processing. However, both the original and improved systems employed a grating monochromator which did not have the spectral resolution or optical efficiency necessary to detect trace amounts of pollutants.

Herget et al reports that these ROSE systems were subsequently further modified to include an interferometer system capable of detecting wavelengths in the infrared spectral region of from 650 to 6000 cm$^{-1}$. This ROSE system could be transported in a van-sized vehicle to a location near the area to be monitored. In this most recent ROSE system, a light source and a source telescope are first positioned at a site remote from the site to be monitored. Energy from this remote light source is collected by a receiver telescope through an opening in the van wall. A tracking mirror reflects the infrared signal of gas(es) emitted from a stack of the facility being monitored into the receiving telescope. The receiving telescope focuses energy from the remote light source and the infrared signal of the gas(es) at the interferometer aperture. The interferometer detector which has a dual element sandwich-type configuration mounted in a liquid nitrogen Dewar scans two infrared regions (i.e. 1800 to 6000 cm$^{-1}$ and 600 to 1800 cm$^{-1}$) separately. Selection of the desired detector element is made by command (via computer). Two beamsplitters are employed in the interferometer. A beamsplitter interchange and realignment takes about five minutes.

This most recent ROSE system has several practical disadvantages. For example, this system employs a stationary source light and source telescope which are positioned in a manner such that the source light is reflected off of the tracking mirror to the receiver telescope. Movement of the tracking mirror to monitor a second nearby site thus necessitates movement of the source light and source telescope if an accurate measurement is to be obtained. This ROSE system is therefore incapable of monitoring more than one site by simply adjusting the tracking mirror. Nor can such system be modified in a simple manner to permit monitoring of several different locations within a few minutes. In fact, Herget et al states that after the initial setup of the ROSE system (which takes two to three hours), subsequent setups in the same vicinity require about one hour under normal conditions.

This newest ROSE system is also incapable of giving precise readings on pollutants which are not in line with or which have already crossed the optical path defined by the remote light source.

Further, pollutants which do not exhibit characteristic infrared peaks in the range of the selected beamsplitter (i.e. either 650–1800 $cm^{-1}$ or 1800 to 6000 $cm^{-1}$) can not be identified without a beamsplitter interchange and realignment. Such interchange and realignment, however, take about five minutes. Consequently, if two pollutants were present in a monitored area simultaneously and one of those pollutants had a characteristic IR band at 1700 $cm^{-1}$ and the other had a characteristic band at 1900 $cm^{-1}$, the ROSE system could not detect and monitor both pollutants simultaneously.

Yet another disadvantage of the ROSE system is the initial set up tie of two to three hours. The length of time required for set up makes the ROSE system almost useless for detecting a leak in its early stages unless the system is permanently installed at the location of the leak or a leak happens to occur during the scheduled monitoring of an area.

Finally, the primary mirrors of the ROSE System are not suitable for continuous exposure to corrosive industrial atmospheres.

Another improved system for monitoring gaseous pollutants is presently being marketed by Bomem Corporation. Detailed information with respect to the construction and operation of this Bomem system are not yet available to Applicants. However, it is apparent from advertising literature for this system that the optical components used in this system and the design of the instrument would not withstand the corrosive atmospheres encountered in many industrial environments.

SUMMARY OF THE INVENTION

It is an object of the present invention to provide a method and apparatus for detecting one or more gaseous materials in the atmosphere o a selected area.

It is also an object of the present invention to provide a method and apparatus for continuously monitoring the atmosphere of a selected area for the presence of any gaseous materials particularly hazardous vapors having suitable absorption or emission peaks in the infrared region.

It is another object of the present invention to provide a method for detecting the amount of infrared absorbing or emitting gaseous materials in the atmosphere of a selected area in which an image of the selected area and the quantity of gaseous material(s) present are simultaneously or sequentially displayed on a monitor.

It is yet another object of the present invention to provide an apparatus capable of detecting the amount of any infrared absorbing or emitting gaseous material in the atmosphere of a selected area and of displaying an image of the selected area and the quantity of gaseous material(s) simultaneously or sequentially on a monitor.

It is a further object of the present invention to provide a method and apparatus capable of detecting the amount and/or presence of any infrared absorbing or emitting material in the atmosphere of a selected area, displaying an image of the area, displaying a significant portion of the infrared spectrum of the radiation coming from the area, and if desired, providing a permanent record of the results, either as a computer file or as a plotter-generated infrared spectrum.

It is a further object of the present invention to provide a method and apparatus capable of detecting the location and limits of a gas cloud of any infrared absorbing or emitting material in a selected area and displaying such information in a form understandable to a monitor or human observer.

It is also an object of the present invention to provide an apparatus capable of detecting the amount and/or presence of any infrared absorbing or emitting material in the atmosphere in which the design and construction of the device is particularly suitable for continuous, automatic, low maintenance, unattended operation in severe industrial environments over extended periods of time.

These and other objects which will be apparent to those skilled in the art are accomplished by collecting the background radiation (both visible and infrared radiation) present in the selected area, analyzing the infrared radiation collected with a suitable spectrometer such as an FTIR spectrometer and making the results of this analysis available in a form understandable to the person or device monitoring the area for the presence of specified gaseous materials. The results of the spectrometric analysis may, for example, be displayed on a video unit or they may be printed, or they may be used to activate a suitable alarm system. In a preferred embodiment, the results of the spectrometric analysis are displayed on a video unit simultaneously or sequentially with the image of the area from which the background radiation had been collected.

Apparatus useful in the practice of this invention must include (a) a radiation collection device capable of collecting both infrared and visible radiation, (b) an interferometer capable of analyzing infrared radiation within a predetermined range of wavelengths collected by radiation collecting device (a) and (c) means for communicating the results of the interferometer analysis being monitored to a monitoring device, an observer or recording device. Such apparatus generally include a large primary energy-collecting mirror having a corrosion resistant surface, optics suitable for collimating and directing the collected energy into a spectrometer, an interferometer of the Michaelson-Morely type, a high-sensitivity infrared detector cooled, for example, by a demand-flow cryostat or solid-state thermoelectric cooler, suitable electronic means for providing high signal-to-noise characteristics, and means for data reduction, display, instrument control and data storage such as a computer and monitor.

In a preferred apparatus for general area monitoring, a computer-controlled turret for aiming the primary energy collection mirror and a video camera for viewing the scene being monitored are employed.

In another preferred configuration, a "hot" mirror may be used to separate the infrared spectrum from the visible spectrum, thus allowing simultaneous viewing of the infrared and visible regions of the exact scene being monitored.

DETAILED DESCRIPTION OF THE INVENTION

The present invention relates to a method for detecting the quantity and/or presence of an infrared absorbing or emitting gaseous material present in the atmosphere of a selected location and to apparatus useful in such detection.

Background radiation is emitted by any object which is at a temperature above absolute zero. A gas present between such an object and a detection device may produce either an emission or an absorption spectrum depending upon the temperature of that gas in relation to the background object or objects. Specifically, if the background object is at a temperature lower than that of the gas, the gas will produce an emission spectrum. Conversely, if the background object is at a temperature higher than that of the gas, the gas will produce an absorption spectrum. If, however, the background object is at the exact same temperature as the gas to be detected, no spectrum is obtainable. The likelihood that the temperature of a background object and the temperature of a gas present in the atmosphere will not differ by at least several tenths of a degree is however extremely remote. A spectrum may therefore be obtained in virtually any environment at a temperature greater than absolute zero.

In principle, it is possible to determine the relative concentration of a particular material in a specific area from the emission or absorption spectrum generated by that material. The precision of such determination is however dependent upon factors such as the particular apparatus employed, the temperature difference between the background object(s) and the particular gaseous material(s), the distance between the area being monitored and the spectrometer, the weather, etc. Under optimum conditions, however, the apparatus of the present invention is capable of detecting a gas at a level as low as 1 part per million per meter.

Figure 1:
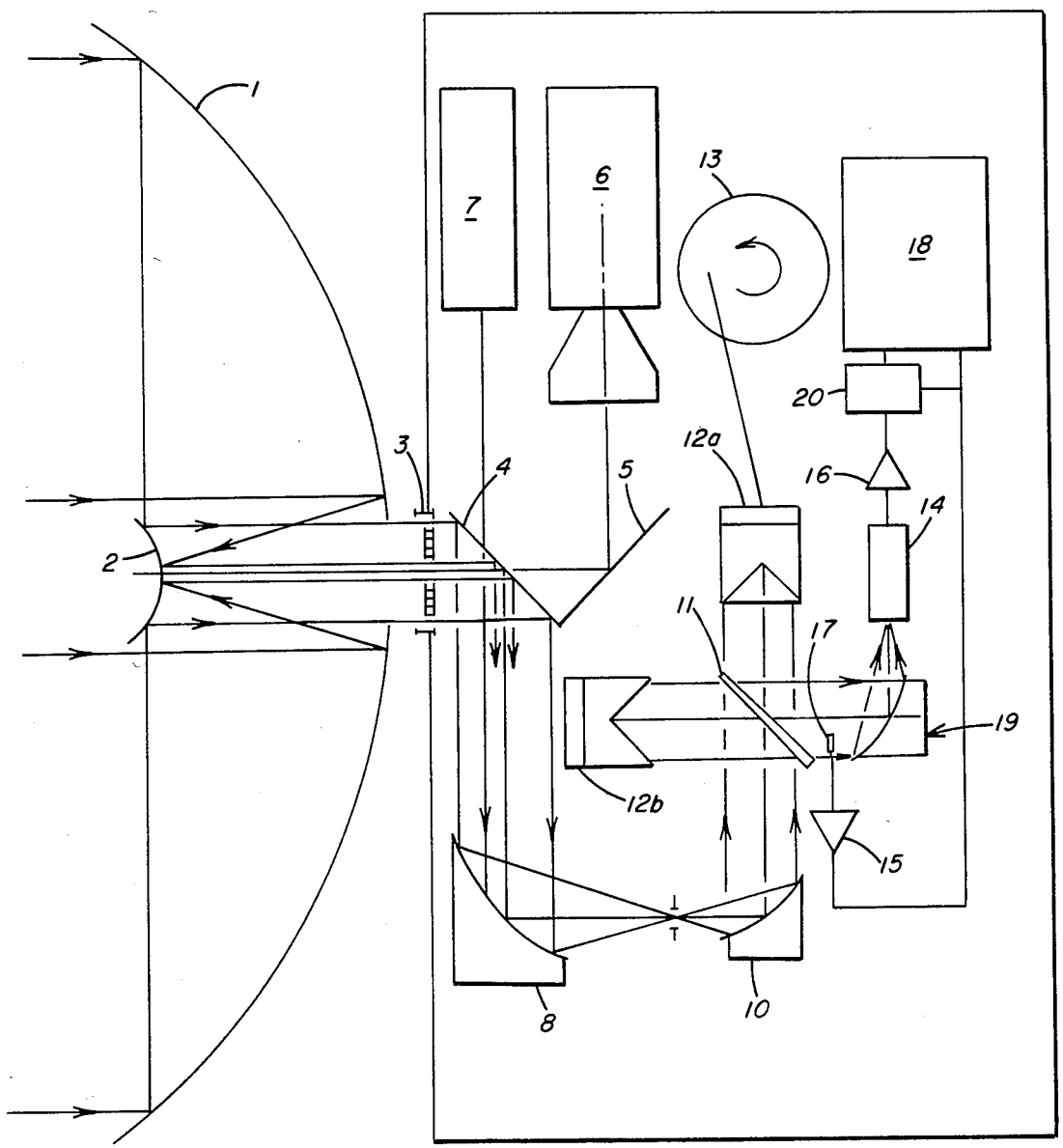
FIG. 1 is a schematic representation of one embodiment of the inventive apparatus.

One embodiment of an apparatus within the scope of the present invention is illustrated in FIG. 1. In the device shown in FIG. 1, the background infrared radiation and visible radiation are collected with a collection device composed of a large concave spherical or paraboloidal reflector (mirror) 1 and a smaller secondary convex spherical or paraboloidal reflector (mirror) 2. Reflector 1 used in this apparatus was made with a nickel substrate electrolytically coated with a highly reflective yet hard, durable, and corrosion resistant rhodium coating. Reflector 2 was a rhodium-plated convex spherical mirror.

A number of reflective coating materials are known and any of them may be used in the apparatus of the present invention, provided they have sufficiently durable and corrosion resistant properties. Because the primary and secondary mirrors are open to the atmosphere, it is desirable that they have protective coatings on the mirror surface which make it possible to clean them and which enhance their corrosion resistance. A rhodium coating is preferred however because it reflects visible and infrared radiation very well, and is resistant to tarnish and oxidation. It is also preferred that the reflectors have a high degree of surface accuracy. That is, the surface should reflect a ray in a manner such that the reflected ray does not deviate substantially from its ideal path It is preferred that any deviation of the reflected ray from its ideal path be no greater than 6 arc minutes.

Although both paraboloidal and spherical mirrors have been used in this collecting device, any mirror having a shape capable of collecting radiation and a surface capable of accurately reflecting visible and infrared radiation may be used.

The visible and infrared radiation collected by reflectors 1 and 2 is passed through a protective window 3 which is transparent to both visible and infrared radiation and then directed onto the "hot" mirror 4. This "hot" mirror separates the infrared radiation from the visible radiation by reflecting the infrared radiation and allowing the visible radiation to pass through to mirror 5 which reflects that visible radiation to video camera 6. An image generated from this visible radiation may then be passed from video camera 6 to a display unit (not shown) such as a television screen.

The protective window 3 used in this apparatus was a clear polyethylene film having a diameter of three inches. The window 3 need not have any specific diameter. It is preferred however that the diameter of window 3 be at least the same as that of reflector 2 and preferably larger than that of reflector 2. A polyethylene window is preferred and was selected because it is transparent in the visible region and has bands in the infrared region which do not interfere with the purpose of the instrument. However, any material which is capable of passing visible light and infrared light in the required regions without a substantial degree of distortion (for example, optical grade zinc selenide plates) may be employed. As can be seen from FIG. 1, protective window 3 is positioned behind and parallel to the small opening in reflector 1. No specific distance between window 3 and the opening of the reflector is required.

The "hot" mirror 4 used in this apparatus was a 4" square mirror made of Pyrex glass having a diameter greater than that of window 3. The mirror as a thin-film coating on the first surface to provide an infrared reflection coefficient of greater than 80%. This "hot" mirror 4 was custom made by Laser Power Optics Corporation. However, any material capable of separating infrared and visible radiation and transmitting one while reflecting the other without a substantial degree of distortion may be used as a "hot" mirror in the apparatus of the present invention.

"Hot" mirror 4 is inclined at an angle such that substantially all of the reflected infrared radiation will reach the reflective surface of reflector 8 and substantially all of the transmitted visible radiation will reach the reflective surface of mirror 5. The optimum angle for a specific device may be readily determined by a few simple preliminary tests. The angle of hot mirror 4 in the device shown in FIG. 1 was 45° (in relation to the perpendicular through window 3).

The mirror 5 may in principle be any reflective surface having an area large enough to reflect sufficient visible radiation to generate a video image of the area being monitored. It is preferred however that mirror 5 be made of a relatively high quality material or have a high quality coating which does not substantially distort the reflected radiation so that a good quality video image be obtained. The mirror 5 in the device illustrated in FIG. 1 was made of glass and had a front surface silver coating. This mirror 5 had dimensions of 4"X 4".

Video camera 6 may be any one of many commercially available video cameras. The camera used in the device shown in FIG. 1 was one sold by Panasonic under the designation WV-1460.

The infrared radiation reflected by "hot" mirror 4 is collimated down to a beam by an off-axis parabolic reflector 8 and smaller off-axis parabolic reflector 10. The off-axis parabolic reflectors which are commercially available from Melles Griot are actually segments cut from regular paraboloidal reflectors which present a circular cross-section when viewed along the mechanical axis. Each of the reflectors 8 and 10 had an electroformed nickel substrate and an electrolytically deposited rhodium surface. These rhodium coated off-axis parabolic reflectors are preferred and were chosen because when they are positioned properly, reflected rays do not deviate from their ideal direction(s) by more than 6 arc minutes. However, other mirrors, such as diamond turned metal mirrors would also be suitable. In fact, any reflective surface in which the optical or symmetry axis of the reflector segment does not pass through the reflector segment itself but instead passes nearby in space and which reflects radiation without substantial distortion may be used.

It is apparent from FIG. 1 that the diameter of off-axis parabolic reflector 10 is smaller than that of off-axis parabolic reflector 8. In the device shown in FIG. 1, reflector 8 had a 3 inch diameter and reflector 10 had a diameter of two inches. The three inch diameter of reflector 8 was chosen to correspond to the diameter of protective window 3 in order to permit reflector 10 to receive substantially all of the infrared radiation which passed through that window 3. The two inch diameter of reflector 10 was selected to correspond to the aperture of beamsplitter 11. In principle, however, any reflectors with diameters (widths) which are capable of receiving and reflecting enough infrared radiation for a spectrometric analysis without substantial distortion may be used.

The beam of infrared radiation is then transmitted from reflector 10 to beamsplitter 11. The beamsplitter 11 used in this apparatus was a ZnSe beamsplitter having a diameter of three inches. However, any of the known commercially available beamsplitters having an appropriate diameter and the ability to split infrared radiation may be used. A wedge-shaped beamsplitter is preferred over a flat plate beamsplitter due to the ease of optical alignment which it affords. In FIG. 1, a $\frac{1}{2}$° wedge was used, but a wedge having any angle which allows separation of reflected radiation from the front and back surface of the beamsplitter could be used advantageously.

A portion of the beam of infrared radiation is then reflected by beamsplitter 11 to retroreflector 12b which is a corner cube retroreflector. Retroreflector 12b reflects that beam back through the beamsplitter 11 to the off-axis parabolic reflector 19. Simultaneously, a second portion of the infrared beam is transmitted through beamsplitter 11 to retroreflector 12a (also a corner cube retroreflector) which reflects that beam back to the beamsplitter 11 which reflects it to the off-axis parabolic reflector 19. Each of the retroreflectors 12a and 12b is a hollow-corner cube construction of three coated optical flat plates assembled into a mutually orthogonal corner. The retroreflectors used in the device shown in FIG. 1 had a gold coating with a silicon oxide protective overcoat, an aperture of 2.5 inches and a 0.5 second of arc accuracy. However, reflectors with any other coating (e.g., aluminum) which will permit reflection of the infrared radiation without substantial distortion would be suitable. Corner cube retroreflectors are preferred because of the ease with which they may be properly aligned. However, in principle, any reflective surface which would reflect infrared radiation without substantial distortion could be used as retroreflector 12a and/or 12b. Because reflective surfaces such as flat plate mirrors are difficult to align properly and improper alignment results in a poor interferogram, use of flat plate mirrors is not recommended.

In FIG. 1, the retroreflector 12a is mounted on a motor driven moveable stage (not shown) for generation of the interferogram. The stage could be mounted on retroreflector 12a or 12b. A constant speed motor and gear train is used to drive the circular cam 13 for the mirror stage at about 72 rpm. The cam moves the precision roller-bearing stage back and forth in a smooth reciprocating motion through about 1 inch of travel. This arrangement was selected to provide a rugged, trouble-free mechanism for generating the interferogram. Other systems such as constant-velocity, voice-coil driven air bearing stages, may be used but they do not provide equivalent mechanical durability. The distance of travel of the moveable stage may be varied, but that distance must be long enough to obtain the desired degree of spectral resolution. In the instrument shown in FIG. 1, one inch of travel in the moveable stage provided better than 1 cm$^{-1}$ of spectral resolution. The period of reciprocation and distance of stage travel are selected to match the characteristics of the active electronic filters in the detector preamplifier 16. This arrangement allows a high signal-to-noise ratio to be achieved without time-averaging several interferograms or spectra. High resolution spectra may therefore be obtained in a minimum amount of time. For example, spectra can be obtained in less than 2 seconds under typical operating conditions. For simplicity and durability, it is preferred to operate the mirror stage 13 with a fixed period and distance of travel. However, other systems which vary the velocity and travel under controlled conditions may also be used very effectively.

In the device illustrated in FIG. 1, mirror movement may be determined by means of laser 7. More specifically, laser 7 inserts a beam with a characteristic wavelength suitable for determination of the mirror position by means of interference fringe counting techniques through "hot" mirror 4. This laser beam is reflected in the same manner as the collected infrared radiation until it passes through beamsplitter 11. Laser detector 17 picks up the interference pattern from the recombined laser beams and transmits the resulting signal to laser preamplifier 15 which clocks a counting circuit used to trigger the start of data conversion and collection.

The off-axis paraboloid reflector 19 is identical to off-axis paraboloid reflector 8 although it is not necessary that these reflectors be the same.

The two infrared beams generated by beamsplitter 11 are then reflected by the off-axis paraboloid reflector 19 to the infrared detector 14 which is maintained at an appropriate temperature (e.g. 75–80° K.). Any commercially available infrared detector having suitable sensitivity and frequency response may be used. In the apparatus illustrated in FIG. 1, a high quality HgCdTe infrared detector mounted in a glass Dewar with a miniature cryostat was used. The cryostat and Dewar were fixed in an aluminum housing with cable for signal output. A silicon diode temperature sensor monitors the cryostat performance. The cryostat is operated with high pressure nitrogen gas. Temperatures lower than ambient temperatures are preferred because the sensitivity of the detector is greater at cooler temperatures (e.g. 75–80° K.). Any other suitable cooling device or technique may be used in accordance with the present invention.

The detector 14 used in the apparatus illustrated in FIG. 1 was a photoconductive HgCdTe detector capable of detecting infrared radiation in the 8–14 $\mu$m range which range would include at least one characteristic identifying band for substantially all of the gaseous pollutants expected to be found in the monitored area. However, any of the commercially available detectors with the capability of detecting infrared radiation within a desired range could be used. The preferred infrared range of a particular detector will of course be dependent upon the specific environment being monitored. Detectors capable of detecting infrared radiation in virtually any selected region are commercially available.

The interferogram signal from detector 14 is then transmitted to the infrared detector preamplifier 16. Preamplifier 16 is a low noise electronic amplifier with remote gain control to adjust the interferogram signal to match the dynamic range of the analog-to-digital converter 20. Active electronic filters are used to reject unwanted frequencies coming from the interferometer and thereby significantly improve the signal-to-noise ratio of the final spectrum. Analog-to-digital converter 20 digitizes the interferogram to be sent to Computer 18.

Although Computer 18 was used in the apparatus of FIG. 1, any device capable of reducing the data received from the infrared detector may be used. Possible alternatives to a computer include optical processors and digital processors.

The computer 18 which was used in the apparatus shown in FIG. 1 had been programmed for fast Fourier transform of the collected data but any program which is capable of reducing the collected data to a useful form could be employed. The computer 18 may also be programed to compare the wavelength of the detected infrared radiation with reference wavelengths of the gases expected to be present in the atmosphere being monitored. However, such comparative programming is not essential to the present invention.

Figure 4:
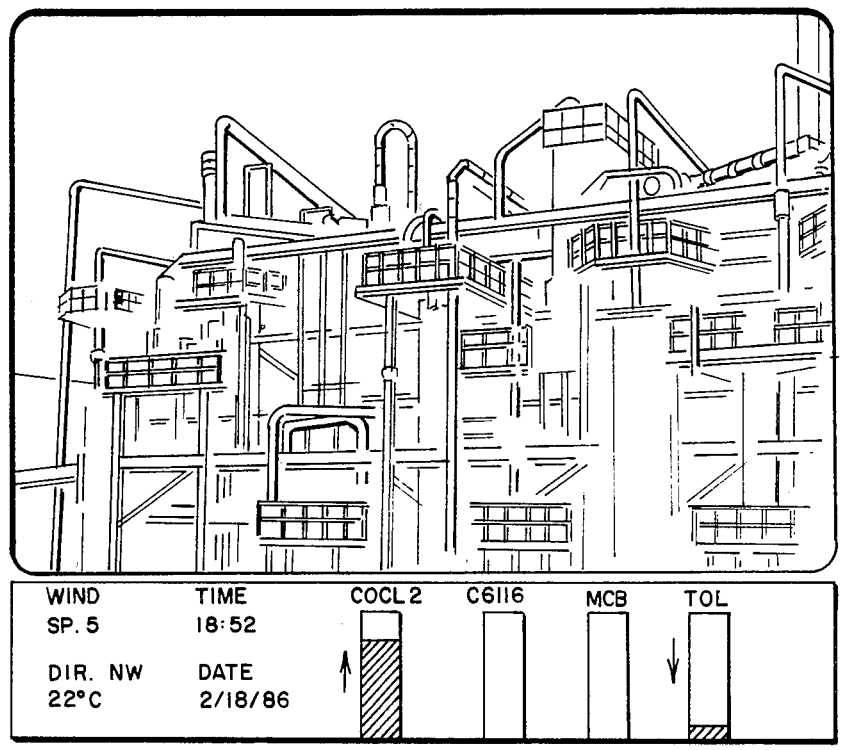
FIG. 4 is an illustration of a video display of the results of an infrared analysis simultaneous with the image of the area to which the analysis pertains of the type obtainable from the apparatus of the present invention.

In a particularly preferred embodiment of the present invention, the computer 18 is programmed to compare measured wavelengths against reference wavelengths and to convert and transmit the results of its analysis in graphic form (e.g. in the form of a bar graph) to a viewing screen on which the visual image of the area being monitored is transmitted by video camera 6. An example of what is seen on the viewing screen where the results of the infrared analysis are displayed simultaneously with the image of the area being monitored is given in FIG. 4. It should be noted that while simultaneous display is preferred, it is also possible to program sequential display of the infrared analysis and video image. It is also possible to program display of the video image and/or infrared spectrum at specified intervals of time. Information gathered and analyzed by the apparatus of the present invention may be used to activate an alarm or trigger an electronic recorder to make a permanent record of the information obtained.

The primary energy gathering reflector 1 is preferably mounted on a computer controlled turret (not shown). This turret makes it possible to scan a 360 degree field of view with a one degree resolution in a manner comparable to a radar tracking system. Such scanning may be "timed" or controlled by any of the methods known in the art. In the device shown in FIG. 1, the areas to be monitored by the apparatus of the present invention may be programmed into the computer 18. Computer 18 will then direct the turret to move to the next pre-programmed position upon receipt of an appropriate signal.

Displacement of the secondary mirror 2 makes it possible to vary the field of view of the instrument. In fact, displacement of the secondary mirror 2 in FIG. 1 by a distance of only 2 inches or less makes it possible to vary the field of view from 0 to 10 degrees. This displacement effect makes wide angle coverage of a normal production operation possible. It also makes it possible to focus the detection apparatus of the present invention in a manner which permits closer coverage of an area in order to identify the source of any leak.

Figure 2:
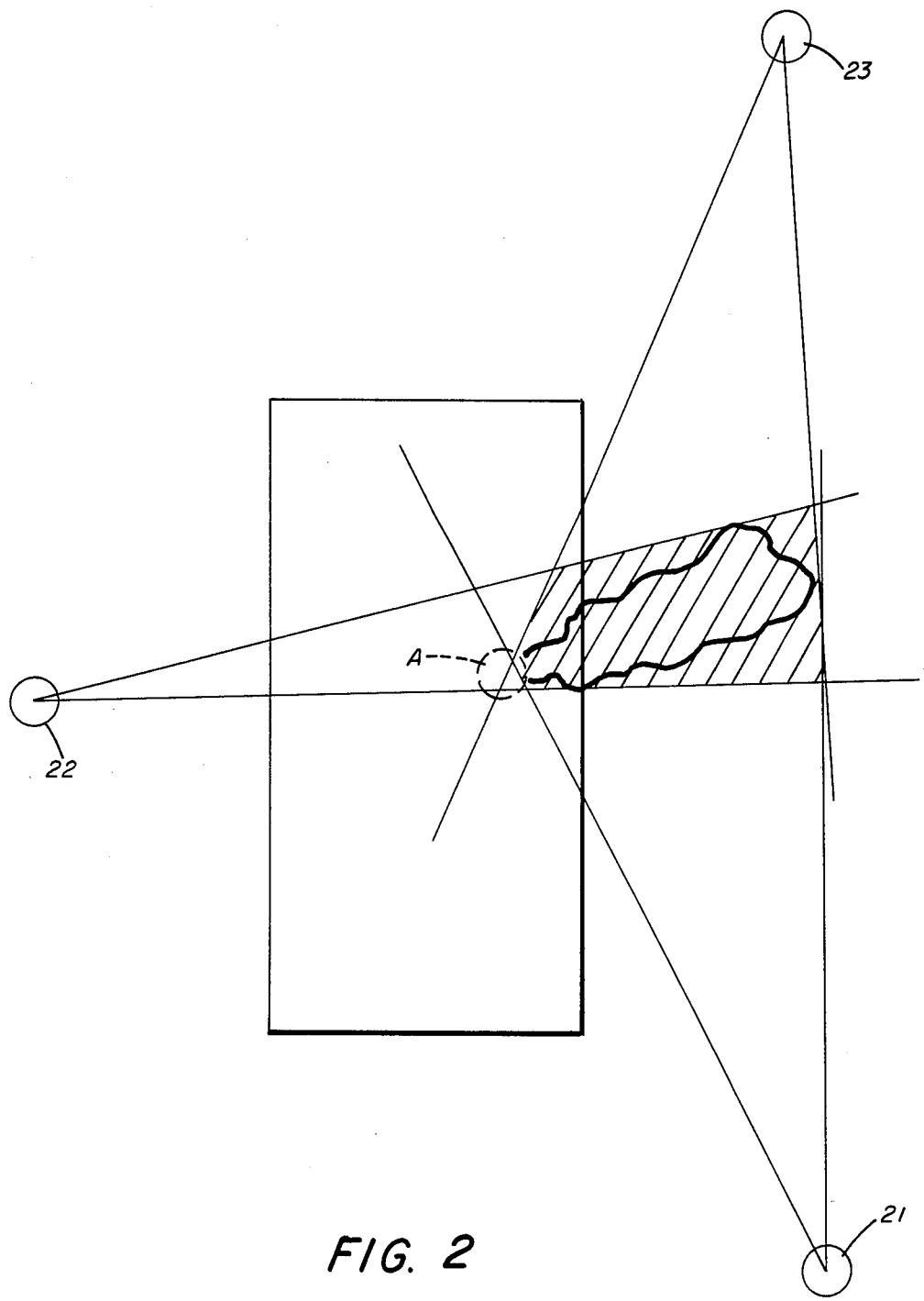
FIG. 2 is a schematic representation of an arrangement of several of the inventive apparatus which arrangement would enable the monitoring of an entire plant and tracking of a gas cloud.

The apparatus of the present invention makes it possible to scan a wide area of a plant on a continuous basis until a leak is detected, discontinue the continuous scan and concentrate the scanning operation on the area in which the leak has been detected by displacing secondary mirror 2 sufficiently to permit a close examination of a specific area. Where the leak is substantial, training the attention of several scanning devices positioned at strategic locations throughout the plant in this manner makes it possible to both follow the location of the gas cloud and to determine its relative concentration. Such information is essential if measures necessary to neutralize that leak are to be taken before the leak becomes a hazard to plant workers and surrounding communities. One such arrangement of several scanning devices is shown in FIG. 2. It is readily apparent from FIG. 2 that triangulation of the data transmitted from detectors 21, 22 and 23 makes it possible to define the area in which the gas cloud generated from the leak at point A is present and to determine the approximate concentration of that gas cloud.

If more than one detector device is employed to monitor a large area e.g., an entire plant, the data from each infrared detector may be transmitted to a central computer directly from the detector or from a smaller computer 18. In like manner, the video images collected at each monitored site may be transmitted directly to a central location. Such centralization is particularly useful in cases in which the path of a gas cloud over a large area is to be followed.

It is also possible to incorporate an alarm system into the apparatus of the present invention which alarm system would be activated by computer 18 whenever a particular pollutant had been detected at a level exceeding a pre-programmed limit. Suitable alarm systems are known in the art and may be readily incorporated into the apparatus of the present invention.

The beamsplitter 11, retroreflectors 12a and 12b, the moving stage and drive mechanism 13, off-axis paraboloid reflector 19, infrared detector 14, infrared detector preamplifier 16, laser 7, laser detector 17, and laser preamplifier 15 are hereafter collectively referred to as the "interferometer". It is preferred that the interferometer be mounted behind primary mirror 1. The preferred method of mounting is on a rigid optical bench which is attached to the body of the instrument by a three-point shock and vibration damped support. This arrangement offers excellent resistance to effects due to ambient temperature changes, vibrations and mechanical stresses. While this is the preferred method of mounting, it is not essential to the present invention and any other means of obtaining a vibration-free, temperature insensitive mounting would be acceptable. The interferometer shown in FIG. 1 covers a continuous band of infrared wavelengths between 8 and 14 $\mu$m. However, the band of wavelengths covered by the interferometer may be varied by selection of a beamsplitter 11 and detector 14 having the capability of covering the desired range. Multiple wavelength bands within the capacity of the beamsplitter may be monitored simultaneously by using several detectors, each of which is useful within a range different from that of the others.

The present invention makes it possible to continuously monitor a wide area for the presence of more than one gaseous material with a single interferometer. In fact, the number of gases present in the atmosphere which may be monitored at any given time is limited only by the capacity of the computer 18 and the requirement that at least one identifiable peak of the compound be present within the spectral range of the instrument. Since virtually every composition which would be monitored by a system of the type of the present invention produces at least one characteristic peak or a combination of peaks within the 3-5 or the 8 to 14 $\mu$m wavelength range, the above-described monitoring apparatus is capable of detecting a wide variety of substances without the expensive narrow band interference filters for each gas to be detected required in many of the known monitoring systems.

The output of the infrared detector 14 is an interferogram which is processed preferably by a fast Fourier Transform Algorithm in computer 18 to produce an emission or absorption spectrum. In addition to the processing of the interferogram, the computer 18 may control the mirror scanning, may analyze the spectrum for peaks corresponding to specified (pre-programed) materials such as toxic gases, may correlate collected data, etc. The result of such analysis may then be printed in a variety of forms and/or projected onto a video display unit.

Figure 3:
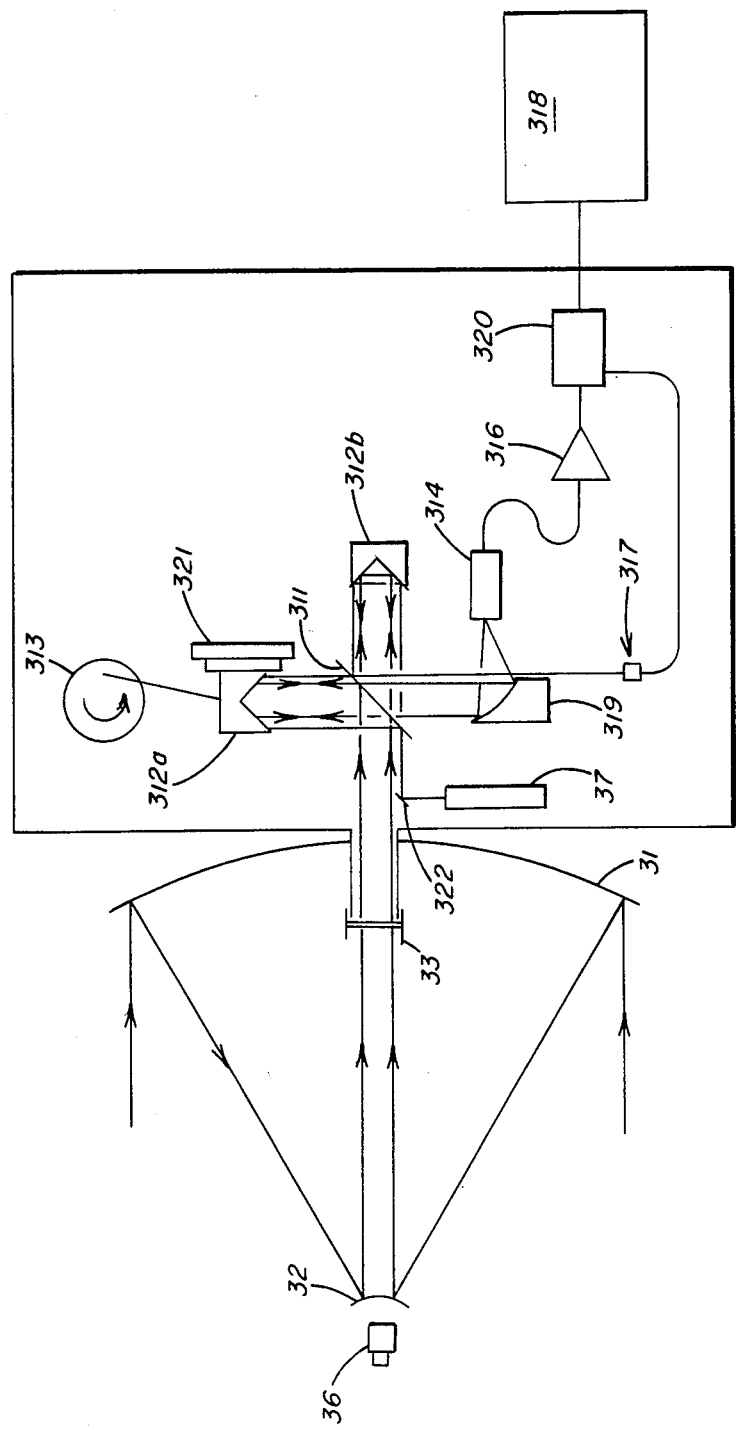
FIG. 3 is a schematic representation of a second embodiment of the inventive apparatus.

FIG. 3 schematically depicts another apparatus useful in the practice of the present invention. In this apparatus, the location of video camera 36 is such that visible radiation is received independently of the infrared radiation to be analyzed. In FIG. 3, camera 36 is positioned in front of the radiation collecting device composed of reflectors (mirrors) 31 and 32. However, camera 36 could also be positioned along or parallel to the axis of the radiation collecting device. In this arrangement, the interferometer need not be equipped with a "hot" mirror because visible radiation from the site being monitored is collected separately from the infrared radiation to be analyzed. With this arrangement, the number of reflecting surfaces and off-axis paraboloid mirrors may be reduced as is apparent from FIG. 3. The protective window 33 may be made from any material which transmits infrared radiation, even those which may be opaque in the visible region. Germanium plates and other such materials could therefore be used. However, windows which transmit in both the infrared and visible regions are preferred because they aid in alignment of the instrument optics. This apparatus also makes it possible to use mirrors 31 and 32 of lower optical quality than mirrors 1 and 2 of the device of FIG. 1 because optical distortion of the video image is no longer a concern in the device depicted in FIG. 3. In all other respects, however, the apparatus shown in FIG. 3 corresponds to the interferometer shown in FIG. 1 in structure and in the mode of operation.

More specifically, reflector 31 of FIG. 3 corresponds to reflector 1 of FIG. 1, reflector 32 of FIG. 3 corresponds to reflector 2 of FIG. 1, and so on through component 320 of FIG. 3 and component 20 of FIG. 1. In FIG. 3, the moving mirror stage 321 for retroreflector 312a is shown. Such a moving stage was discussed with respect to the apparatus of FIG. 1 but was not shown in FIG. 1. Beam steering reflector (mirror) 322 reflects the beam from laser 37 in a manner such that the reflected laser beam is inserted into the infrared radiation collected by reflectors 31 and 32. Reflector 322 may be made from any material having a reflective surface such as an ordinary mirror.

The invention is further illustrated but is not intended to be limited by the following examples.

EXAMPLES

Example 1

An apparatus was assembled from the following components in accordance with the arrangement shown in FIG. 3.

Reflector 31: a concave spherical reflector having a diameter of 36" and a focal length of 60" (sold by Optical Radiation Corp.) coated with rhodium.

Reflector 32: a convex spherical reflector having a diameter of 2" and a focal length of 3" (sold by Ealing Electrooptics Co.) coated with rhodium.

Infrared Window 33: a 0.5 mil thick film of clear polyethylene.

Beamsplitter 311: ZnSe infrared beamsplitter having a 3" diameter and sold by Laser Power Optics Corp.

Reflectors 312a and 312b: Gold surfaced retroreflectors having a 2½" aperaturer which is accurate to ½ second of arc sold by Precision Lapping and Optics Company.

Reflector 319: an off-axis paraboloid reflector having a 2" diameter and sold by Melles Griot.

Infrared Detector 314: A HgCdTe infrared detector mounted in a cryostat cooler sold by Judson Infrared Inc. under the designation Judson J15-DG.

Infrared Detector Preamplifier 316: Preamplifier and active filters of a custom design having a band pass of 3-9 kilohertz and remote gain control.

Analog to Digital Converter 320: 14 bit analog to digital converter sold by Analog Devices Company with designation HAD-1409KM.

Computer 318: An IBM-AT computer sold by IBM Corporation.

HeNe Laser 37: a 1 mw HeNe laser sold by Melles Griot.

Moving Mirror Motor for Cam of Mirror Stage 313: a 72 rpm motor with gear train sold by Oriental Motors Corp. under designation #01K05GK-AA and #OGK6-0KA.

Beam Stearing Mirror 322: A 1" square front surface mirror sold by Daedal Inc. under designation #2805.

Video Camera 36: A video camera sold by Panasonic Corporation under the designation WV-1460.

Moving Mirror Stage 321: A precision roller-bearing stage sold by Automation Gauges under the designation CRK-3.

Laser Detector 317: A PIN Photo Diode #PD50PI sold by Sharp Corporation.

Components 311, 312a, 312b, 319, 314, 316, 320, 37, 313, 322, 321 and 317 were mounted on a shock and vibration damped optical bench mounted behind the primary mirror 31 in a hermetically sealed enclosure.

Approximately 0.1 gm of phosgene was released at an outdoor site of a toluene diisocyanate production facility in which the above-described apparatus was present. A remote infrared source was located approximately 100 meters from the apparatus of the present invention in line with the point of gas release. This apparatus detected the presence of the phosgene and displayed a spectrum of the 8–14 μm infrared region containing absorption peaks characteristic of phosgene in less than 4 seconds. A video image of the scene was simultaneously available and could be viewed to determine the area being monitored. (See FIG. 4).

Example 2

The apparatus used in Example 1 was positioned at an outdoor site aimed in the general direction of plant operating units. No remote infrared source was employed for the test. Approximately 1 gram of dichlorodifluoromethane was released at a distance of 80 meters from the apparatus. The apparatus detected the presence of the chlorofluorocarbon and displayed a spectrum of the 8–14 μm infrared region containing three absorption peaks characteristic of dichlorodifluoromethane in less than 4 seconds. A video image of the scene was simultaneously available and was viewed to determine the area being monitored.

Example 3

The apparatus described in Example 1 was located outdoors at a chemical production facility. A remote infrared source powered by a 250 watt element located at the focal point of a 30 inch parabolic mirror was positioned 200 meters away in an unobstructed line from the apparatus. A gas test cell consisting of a polyethylene cylinder 2 meters long and 40" in diameter with a 1 mil clear polyethylene film stretched over each end was positioned in the beam path approximately 100 meters from the measuring apparatus. A measured amount of a test gas (e.g. phosgene, dichlorodifluoromethane, ammonia, ethylene oxide) was injected into the cylinder and dispersed by means of a small electric fan. Spectra for each gas at each of several concentrations were taken and the peak heights of characteristic absorption bands for each compound were measured and used to construct a calibration curve of concentration as a function of peak height of a characteristic band. Combinations of non-reactive gases gave spectra containing peaks characteristic of both species while combinations of reactive gases showed expected changes in peaks or peak heights commensurate with the stoichiometry of the mixtures. Other means of establishing calibration curves such as placing a short 3" diameter gas cell or a suitable absorption filter in the collimated beam reflected from the secondary energy collecting mirror 32 can also be employed.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for detecting gaseous materials present in the atmosphere of a selected area comprising
    (a) collecting background radiation from the selected area,
    (b) analyzing the collected radiation having infrared wavelengths in a selected region with a spectrometer to detect any gaseous material present in the atmosphere which has a characteristic infrared spectrum in a selected wavelength region,
    (c) providing the results of the analysis of step (b) in a form understandable to a monitoring device or a human observer and
    (d) displaying as an image the visible radiation collected from the selected area.

2. The process of claim 1 in which the background radiation collected in step (a) is separated into a portion composed of radiation having infrared wavelengths and a portion composed of visible radiation.

3. The process of claim 2 in which the selected region of infrared wavelengths is 3–5 μm and/or 8–14 μm.

4. The process of claim 3 in which the analysis is carried out with a Fourier Transform Infrared spectrometer.

5. The process of claim 4 in which the results of the infrared analysis of (b) are provided in accordance with (c) on a video screen.

6. The process of claim 5 in which the visible radiation is displayed in accordance with (d) simultaneously with the infrared analysis results on a video screen.

7. The process of claim 5 in which the visible radiation is displayed in accordance with (d) sequentially with the infrared analysis results on a video screen.

8. The process of claim 1 in which the spectrometer generates an interferogram in (b) which interferogram is processed by active electronic filters to improve the signal-to-noise ratio.

9. The process of claim I in which the results of the infrared analysis of (b) are provided on a video screen in step (c).

10. The process of claim 1 in which the infrared analysis of (b) and visible radiation image are displayed simultaneously or sequentially on a single video screen.

11. The process of claim 1 in which the infrared analysis of (b) and visible radiation image are displayed simultaneously on two video screens.

12. The process of claim 1 in which the selected region of infrared wavelengths is 3–5 μm.

13. The process of claim 1 in which visible radiation present in the selected area is collected by a video camera and background radiation including both infrared and visible radiation segments is collected by a reflective device.

14. The process of claim 13 in which the visible radiation collected by the video camera is collected prior to collection of the background radiation by a reflective device.

15. The process of claim 1 in which the background radiation from the selected area is collected from several different locations.

16. The process of claim 15 in which the results of the analyses of the infrared radiation are transmitted to a central data reduction device which correlates those results.

17. The process of claim 1 which is carried out on a continuous basis.

18. The process of claim 1 in which the area in which the gaseous materials are to be detected is changed at regular intervals.

19. The process of claim 1 in which the infrared analysis of (b) and visible radiation image are displayed sequentially on a single video screen.

20. The process of claim 1 in which the selected region of infrared wavelengths is 8–14 $\mu m$.

21. The process of claim 1 in which the selected region of infrared wavelength is 3–5 and 8–14 $\mu m$.

22. An apparatus for monitoring the atmosphere of a selected area for the presence of gaseous materials comprising
   (a) a radiation collection device capable of collecting both infrared and visible radiation,
   (b) a video camera,
   (c) an interferometer capable of analyzing infrared radiation within a predetermined range of wavelengths collected by radiation collecting device (a) and
   (d) means for communicating the results of the interferometer analysis and a video image of the area being monitored.

23. The apparatus of claim 22 in which the radiation collection device is a concave electroformed mirror with a rhodium surface.

24. The apparatus of claim 23 in which the interferometer (c) is composed of
   (1) a beamsplitter capable of splitting infrared radiation within a predetermined range of wavelengths positioned to receive the infrared radiation,
   (2) a first retroreflector positioned to receive radiation reflected by beamsplitter (1),
   (3) a second retroreflector positioned to receive radiation transmitted by beamsplitter (1),
   (4) a retroreflector support capable of moving retroreflector (2) or (3) in a reciprocating motion,
   (5) an off-axis paraboloid reflector positioned to receive combined infrared beams coming from the beamsplitter (1), and
   (6) an infrared detector positioned to receive infrared radiation from reflector (5).

25. The apparatus of claim 24 in which the retroreflector support is moved at a fixed reciprocating period such that a narrow band width interferogram containing information from the 3–5 $\mu m$ or 8–14 $\mu m$ infrared region is generated.

26. The apparatus of claim 25 in which the narrow band width interferogram is processed by active electronic filters to improve the signal-to-noise ratio of the interferogram.

27. The apparatus of claim 24 in which beamsplitter (3) is capable of splitting infrared radiation in the 3–5 $\mu m$ and/or 8–14 $\mu m$ range.

28. The apparatus of claim 27 in which retroreflectors (2) and (3) are corner cube retroreflectors.

29. The apparatus us of claim 27 in which infrared detector (6) is cryostatically cooled.

30. The apparatus of claim 27 in which the infrared detector is thermoelectrically cooled.

31. The apparatus of claim 24 in which retroreflectors (2) and (3) are corner cube retroreflectors.

32. The apparatus of claim 24 in which hot mirror is positioned between the radiation collection device and the interferometer.

33. The apparatus of claim 32 in which visible radiation transmitted through the hot mirror is received by a video camera.

34. The apparatus of claim 24 in which the video camera is positioned in front of radiation collection device (a) to collect visible radiation from the site being monitored.

35. The apparatus of claim 24 in which (d) is a computer programed to analyze an interferogram for the presence of one or more gaseous materials or concentration thereof.

36. The apparatus of claim 35 in which the computer is also programmed to control scanning of more than one preselected location on a continuous basis.

37. The apparatus of claim 22 in which a hot mirror is positioned between the radiation collection device and the interferometer.

38. The apparatus of claim 37 in which visible radiation transmitted through the hot mirror is received by a video camera.

39. The apparatus of claim 22 in which (d) is a computer programmed to analyze an interferogram for one or more gaseous materials and concentration thereof.

40. The apparatus of claim 39 in which the computer is also programmed to control scanning of more than one preselected location on a continuous basis.

41. The apparatus of claim 22 in which the video image and analysis of infrared radiation are simultaneously displayed on a viewing screen.

42. The apparatus of claim 22 in which the radiation collection device is a concave diamond-turned mirror with a rhodium surface.

43. The apparatus of claim 22 in which the video image and analysis of infrared radiation are sequentially displayed on a viewing screen.

* * * * *